United States Patent [19]
Shipstead

[11] Patent Number: 5,718,673
[45] Date of Patent: Feb. 17, 1998

[54] FOOT SUPPORT DEVICES AND METHODS

[76] Inventor: Clare Shipstead, 892 Pine Grove Ave., Traverse City, Mich. 49686

[21] Appl. No.: 692,698

[22] Filed: Aug. 6, 1996

[51] Int. Cl.$^6$ ........................................................ A61F 5/00
[52] U.S. Cl. ............................ 602/27; 602/16; 602/33
[58] Field of Search ............................ 602/5, 23, 27–29, 602/61, 62, 65, 66, 16, 33; 128/882, 889, 892–894

[56] References Cited

U.S. PATENT DOCUMENTS

| | | | |
|---|---|---|---|
| 1,595,087 | 8/1926 | Gibson | 602/66 X |
| 1,930,188 | 10/1933 | Arthur | 602/66 |
| 1,974,045 | 9/1934 | Frei | 602/66 |
| 3,527,209 | 9/1970 | Baker | 602/28 |
| 4,329,982 | 5/1982 | Heaney | 602/28 |
| 4,345,590 | 8/1982 | Nakajima | 602/65 |
| 4,982,733 | 1/1991 | Broadhurst et al. | 602/27 |
| 5,257,969 | 11/1993 | Mance | 602/28 |
| 5,399,155 | 3/1995 | Strassburg et al. | 602/28 |
| 5,472,411 | 12/1995 | Montag et al. | 602/27 X |
| 5,475,935 | 12/1995 | Frost | 602/27 X |

*Primary Examiner*—Jerome Donnelly
*Attorney, Agent, or Firm*—Charles M. Kaplan

[57] ABSTRACT

Foot supporting devices and methods hold the wearer's foot and leg at a predetermined angle for sufficient time to reduce foot fatigue or pain, while the wearer is not on the feet. The invention requires that there be no part of the foot supporting devices making contact with or causing stress on the wearer's heel. The foot supporting devices may be made from soft, pliable fabric materials.

16 Claims, 3 Drawing Sheets

FOOT SUPPORT DEVICES AND METHODS

BACKGROUND OF THE INVENTION

This invention relates to devices and methods for supporting human feet, and more particularly to trusses that can be used to diminish or eliminate the pain from foot ailments and fatigue. In particular, people with heel spurs (plantar fasciitis) often suffer pain after they have been on their feet for long periods of time while working, walking or exercising. Heel spurs often cause pain for people who exercise by running or jogging. Such pain is often severe when the person with heel spurs first stands up after a nights sleep in bed or after a long period of rest off of the feet. Prior foot support braces often aggravate the pain or discomfort of people with heel spurs when such devices contact or exert pressure against the wearer's heel. Also, prior foot support braces are cumbersome and can not be worn when the user is sleeping.

OBJECTIVES OF THE INVENTION

Accordingly, it is an object of tins invention to provide improved methods and devices for relieving foot pain, discomfort and fatigue.

Another object is to provide pain relieving methods and devices that should be worn when a person sleeps or when the person is at rest and off of the feet.

A further object is to provide adjustable soft, limp, fabric trusses that can hold the wearer's foot at a predetermined angle comfortably for sufficient time to relieve foot pain or fatigue.

Another object is to provide pain and fatigue relieving methods and foot trusses that are not to be worn when the wearer has shoes on, and which do not contact or cause stress on the wearer's heel.

A still further object is to provide adjustable, light weight, durable, washable pain relieving foot trusses that can be inexpensively made from commonly available fabric materials, that do not have to be fitted specifically for any individual person before they can be worn, and which do not have defects found in similar prior art foot aid devices.

A further object is to provide methods of holding a person's foot at a predetermined angle with respect to the person's leg for sufficient time to relieve foot discomfort or pain without contacting the person's heel and without causing muscle tension in the person's leg or foot.

Another object is to provide foot strain and pain relief methods and devices that do not aggravate heel spurs.

Other objects and advantages of the methods and foot aid devices incorporating this invention will be found in the specification and claims, and the scope of the invention will be set forth in the claims.

DESCRIPTION OF THE INVENTION

Figure 1:
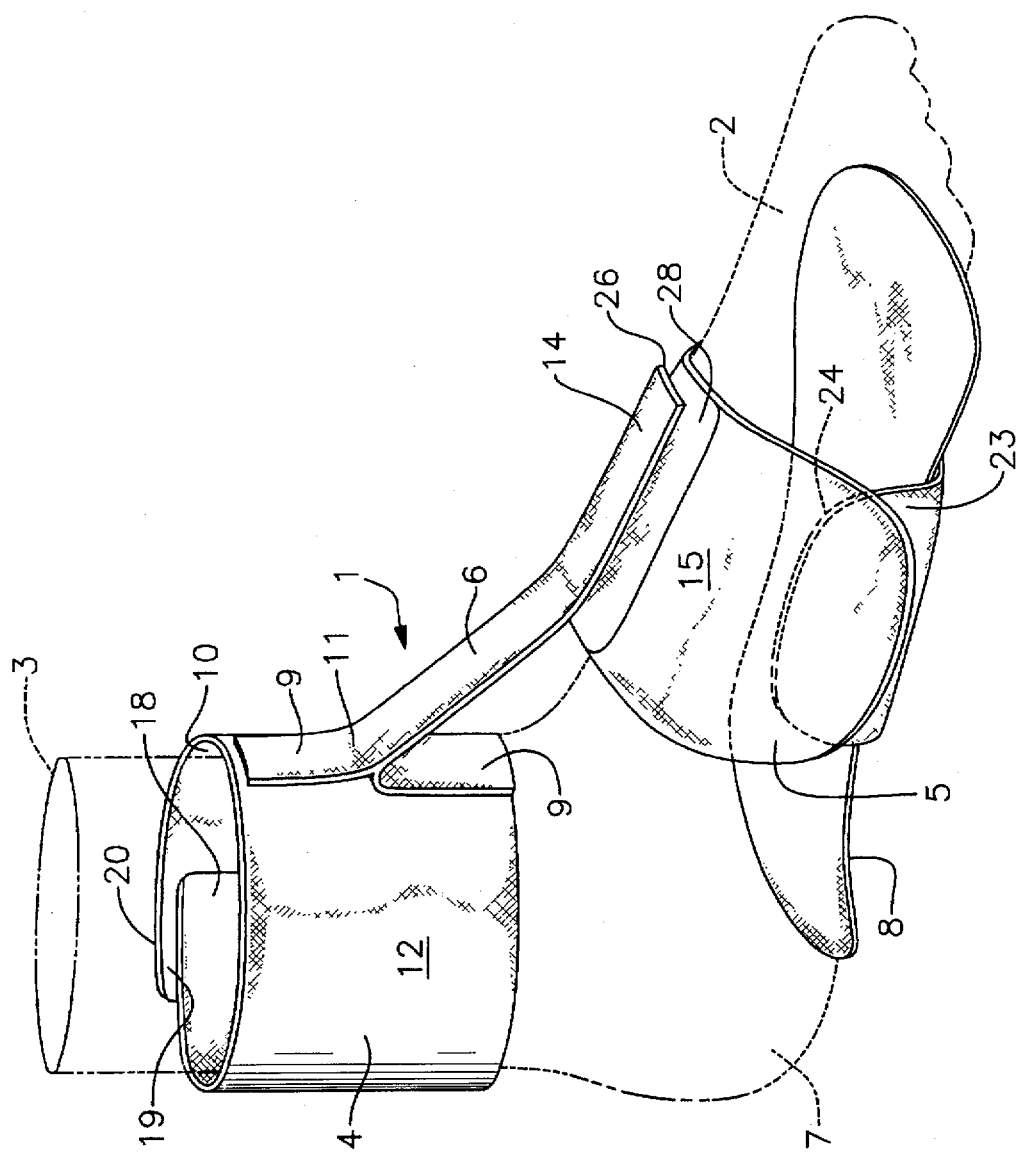
FIG. 1 is a schematic, perspective view of a preferred embodiment of this invention.
Figure 2:
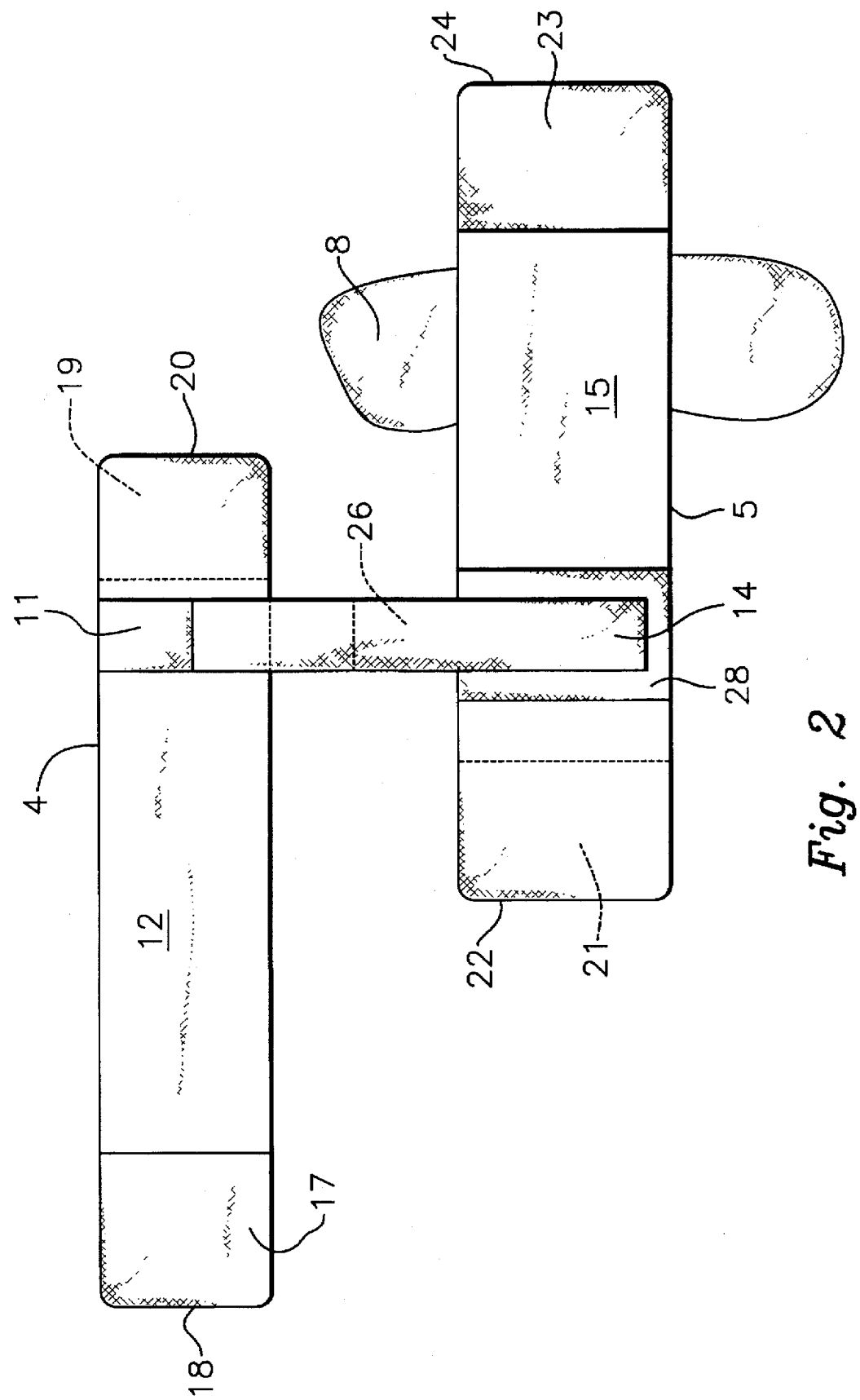
FIG. 2 is a top plan view of the embodiment of FIG. 1 when opened and spread out.
Figure 3:
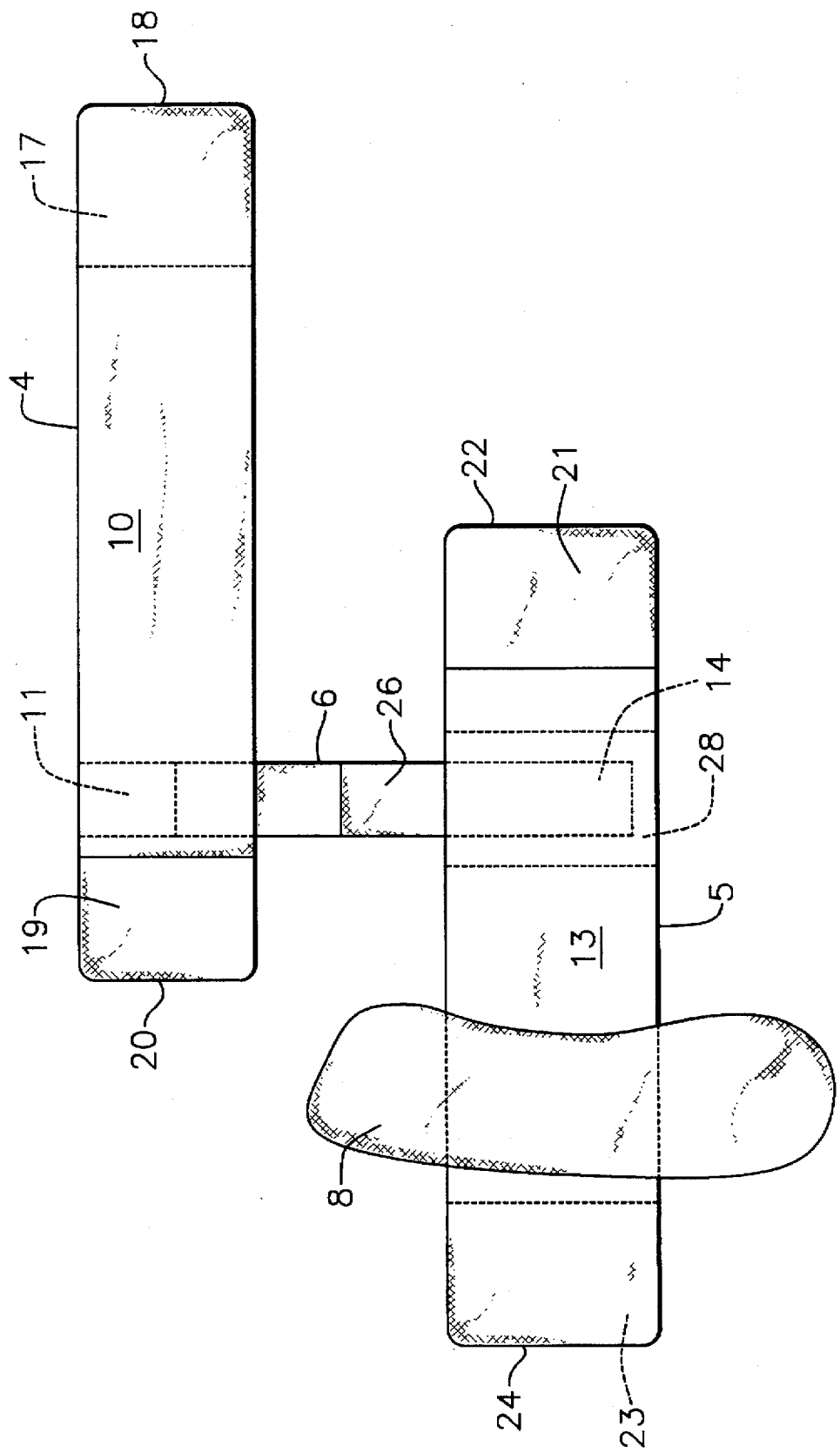
FIG. 3 is a bottom view of the embodiment of FIG. 1 as shown in FIG. 2.

The drawing shows an adjustable, fabric, soft, limp, foot supporting truss 1 embracing the foot 2 and leg 3 (shown in broken lines of its wearer. The truss comprises a first strap 4 of sufficient length to encircle the wearer's leg 3 above the ankle. A second strap 5 is of sufficient length to encircle the wearer's foot 2 at about the center of the foot in the area of the instep and arch. A third strap 6 connects the first and second straps between the instep and the leg on the side opposite to the heel 7. preferably a conventional arch support pad 8 is placed between second strap 5 and the bottom of the arch of the foot 2, although the pad 8 is not essential. No part of the truss 1 touches or puts a strain on the heel 7 of the wearer.

The first and second straps are adjustable so that the truss 1 can fit a large number of people of different sizes. The inner surface 10 of the first strap 4 is the surface that contacts the leg 3 of the wearer. The third strap 6 is bifurcated at one end 11 and the bifurcated end portions 9 are sewn to the opposite surface 12 of the strap 4. The inner surface 13 of the second strap 5 is the surface that contacts the foot 2 of the wearer, and the opposite end 14 of the third strap 6 is releasably connected to the opposite surface 15 of the strap 5. The straps 3, 5, and 6 may be made from any durable, light weight, soft, limp, washable fabric material, preferably, the first and second straps 3 and 5 are made from washable ACTION elastic webbing two inches in width. Third strap 6 may be made from either elastic or non-elastic washable webbing having a smaller width.

The first and second straps 3 and 5 each include means for releasably connecting their respective ends for permitting their length to be adjusted to fit the specific wearer of the truss 1. preferably the mating segments of conventional hook and loop fasteners are attached to the opposite surfaces at the opposite ends of each of the first and second straps. First strap 4 has a hook and loop segment 17 attached to its surface 12 at one end 18 and a mating hook and loop segment 19 attached to its surface 10 at the opposite end 20. Second strap 5 has a hook and loop segment 21 attached to its surface 13 at one end 22, and a mating hook and loop segment 23 attached to it surface 15 at the opposite end 24.

The third strap 6 employs means for permitting its length to be adjusted to fit the specific wearer of the truss 1. preferably a hook and loop fastener segment 26 is attached to the opposite end 14 of the strap 6 for mating with a hook and loop fastener segment 28 attached to the surface 15 of the strap 5 intermediate the ends 22 and 24 of that strap. Alternatively, third strap 6 may be sewn at its end 14 to second strap 5, in which case the mating hook and loop fastener segment 26 would be located at its end 11 and the segment 28 would be located on the surface 12 of first strap 4. It is also possible to located hook and loop fastener segments at both of the ends 11 and 14 of third strap 6 for mating with hook and loop fastener segments located intermediate the end of both of straps 4 and 5.

Although hook and loop fasteners are preferred as the means for adjusting the lengths of straps 4, 5, and 6, any other conventional separable fasteners such as buckles and snap fasteners may be used. The only requirement is that the fasteners permit circumferential or lengthwise adjustment of the straps so that the straps can snugly encircle and fit the different sizes of the legs and feet of the various wearers of the truss 1.

A person at rest (i.e. when lying or sitting down with essentially no weight on the feet) can obtain relief from foot discomfort by practicing the methods of using the truss 1 disclosed herein. This can be accomplished by snugly enclosing a portion of a wearer's leg 3 above the ankle with first strap 4, and snugly enclosing a portion of the wearer's foot 2 at the arch and instep with second strap 5. When a normal foot and leg are relaxed, they make an angle of more than 90° with respect to each other. The methods of using the truss 1 include the step of connecting straps 4 and 5 with third strap 6 so as to exert tension in the strap 6 of about one to three pounds that draws the enclosed portions of the foot and leg toward each other to relative positions that the foot and leg could not achieve without muscle tension while the person using truss 1 is at rest. The strap 6 should be used to hold the person's leg and foot at an angle of about 90° without touching such person's heel, and without tension in the muscles of the foot and leg, for at least about ten minutes. Optimum benefit may be obtained by holding the leg and foot at such an angle without muscle tension for about six to eight hours, preferably while the person using truss 1 sleeps. This has been demonstrated to relieve aches caused by tired feet and muscles and the pain caused by heel spurs.

While the present invention has been described with reference to particular embodiments of foot supporting devices, it is not intended to illustrate or describe all of the equivalent forms or ramifications thereof. Also, the words used are words of description rather than limitation, and various changes may be made without departing from the spirit or scope of the invention disclosed herein. It is intended that the appended claims cover all such changes as fall within the true spirit and scope of the invention.

What I claim as new and desire to secure by Letters Patent of The United States is:

1. A foot supporting truss for use when its wearer is at rest, comprising:
   A. a first substantially rectangular strap of sufficient length for encircling and contacting the wearer's leg above the ankle, and means for releasably connecting and disconnecting terminal ends of said first strap to each other around the wearer's leg above the ankle in a manner that enables said first strap to contact the wearer's leg above the wearer's ankle but prevents said first strap from touching the heel of the wearer;
   B. a second substantially rectangular strap of sufficient length for encircling and contacting the wearer's foot adjacent its instep and arch, said second strap having unattached free terminal ends, and means for releasably connecting and disconnecting said free terminal ends of said second strap to each other around the wearer's foot adjacent its instep and arch in a manner that enables said second strap to contact the wearer's foot adjacent the wearer's arch and instep but prevents said second strap from touching the heel of the wearer;
   C. a releasable third strap of adjustable length for connecting and disconnecting said first and second straps to each other above the wearer's foot without touching heel of the wearer, said third strap being under tension so as to draw the wearer's foot toward the wearer's leg, without causing pressure on the wearer's heel, to a position the foot could not occupy without muscle tension when the wearer is at rest;
   D. an unattached elongated arch supporter adapted to be held against the bottom of the wearer's foot by said second strap: and
   E. there being no part of said truss or said arch supporter contacting the heel of the wearer so as to cause or exert pressure on the wearer's heel.

2. The foot supporting truss defined in claim 1, wherein said means for releasably connecting said straps comprises hook and loop connectors.

3. The foot supporting truss defined in claim 1, wherein said third strap is permanently attached at one end to either of said first and second straps, said third strap having a hook and loop connector secured to its other end, and the other of said first and second straps having a hook and loop connector for mating with said hook and loop connector on said third strap attached intermediate its ends.

4. The foot supporting truss defined in claim 1, wherein said first strap has an inside surface for contacting the wearer's leg and an opposite surface facing away from said leg, said second strap has an inside surface for contacting the wearer's foot and an opposite surface facing away from said foot, and said third strap connects said outside surfaces of said first and second straps.

5. The foot supporting truss defined in claim 1, wherein said tension in said third strap is about one to three pounds.

6. A heel spur truss for relieving foot discomfort from plantar fasciitis for use when its wearer is at rest lying or sitting down with essentially no weight on the person's foot, comprising:
   A. a first strap having sufficient length to encircle and contact the wearer's leg above the wearer's ankle, and separable fastener means for releasably connecting and disconnecting terminal ends of said first strap to each other around the wearer's leg above the ankle in a manner that enables said first strap to contact the wearer's leg above the wearer's ankle but prevents said first strap from touching the heel of the wearer;
   B. a second strap having sufficient length to encircle and contact the wearer's foot adjacent the wearer's arch and instep, said second strap having unattached terminal free ends, and separable fastener means for releasably connecting and disconnecting said unattached terminal free ends of said second strap to each other around the wearer's foot adjacent the wearer's arch and instep in a manner that enables said second strap to contact the wearer's foot adjacent the wearer's arch and instep but prevents said second strap from touching the heel of the wearer;
   C. a releasable third strap of adjustable length for connecting and disconnecting said first and second straps to each other above the wearer's foot without touching the heel of the wearer, said third strap being under tension that draws the wearer's foot toward the wearer's leg, without causing pressure on the wearer's heel, to a position the foot could not occupy without muscle tension when the wearer is at rest;
   D. an arch supporter adapted to be held against the bottom of the wearer's foot adjacent the arch of the foot by said second strap; and
   E. there being no part of said truss or said arch supporter contacting the heel of the wearer so as to cause or exert pressure on the wearer's heel.

7. The heel spur truss defined in claim 6, wherein said first, second and third straps are made from soft, limp fabric material; said first strap has an inside surface for contacting the wearer's leg and an opposite surface facing away from said leg; said second strap has an inside surface for contacting the wearer's foot and an opposite surface facing away from said foot; said third strap connects said outside surfaces of said first and second straps, and said tension in said third strap is sufficient to hold said foot at an angle of about 90° with respect to the wearer's leg.

8. The method of relieving foot discomfort from plantar fasciitis while a person is at rest lying or sitting with essentially no weight on the person's foot, comprising the steps of:
   A. providing a first substantially rectangular strap and encircling and contacting a portion of the person's leg above the ankle with said first strap without touching or exerting pressure on the person's heel;

B. providing a second substantially rectangular strap and encircling and contacting a portion of the person's foot adjacent the arch and instep with said second strap without touching or exerting pressure on the person's heel;

C. providing an elongated arch supporter and inserting said contacted portion at the bottom of the person's foot adjacent the arch;

D. providing a third strap that does not touch or exert pressure on the person's heel and exerting tension that draws the encircled and contacted portions of the foot and leg toward each other to relative positions that said foot and leg could not achieve without muscle tension while the person is at rest by connecting said first and second straps and pulling said first and second straps toward each other above the person's foot with said third strap; and E. holding said encircled and contacted portions of said leg and foot in said relative positions without muscle tension and without touching or exerting pressure on the person's heel for a sufficient length of time to relieve the foot discomfort from plantar fasciitis.

9. The method of relieving foot discomfort while a person is at rest as defined in claim 1, comprising maintaining said tension in the range of about one to three pounds.

10. The method of relieving foot discomfort while a person is at rest as defined in claim 1, comprising maintaining said foot and leg in said relative positions for at least about ten minutes.

11. The method of relieving foot discomfort while a person is at rest as defined in claim 8, comprising maintaining said foot and leg in said relative positions for from about ten minutes to about eight hours.

12. The method of relieving foot discomfort while a person is at rest as defined in claim 8, further comprising exerting tension in the range of about one to three pounds that draws the encircled portions of the foot and leg toward each other to relative positions of about 90°, and holding said portions of said leg and foot in said relative positions for at least ten minutes without touching such person's heel.

13. The method of relieving foot discomfort while a person is at rest as defined in claim 12, comprising maintaining said foot and leg in said relative positions of about 90° for from about ten minutes to about eight hours.

14. The method of relieving foot discomfort from plantar fasciitis defined in claim 8 further comprising, encircling and contacting a portion of the person's foot adjacent the arch and instep with said second strap by overlapping unattached free terminal ends of said second strap and connecting said unattached free terminal ends by engaging separable fasteners that are secured to said unattached free terminal ends of said second strap.

15. The foot supporting truss defined in claim 1, wherein said second strap consists only of a unitary length of fabric material having two free terminal ends.

16. The heel spur truss defined in claim 6, further comprising said separable fastener means of said first and second straps comprising hook and loop connectors, said third strap being permanently attached at one of its ends to either of said first and second straps, said third strap having a hook and loop connector at its other end, and the other of said first and second straps having a hook and loop connector intermediate its ends for mating with said hook and loop connector on said other end of said third strap.

* * * * *